(12) United States Patent
Kluger et al.

(10) Patent No.: US 11,911,503 B2
(45) Date of Patent: *Feb. 27, 2024

(54) MANUFACTURING OF SEMI-PLASTIC PHARMACEUTICAL DOSAGE UNITS

(71) Applicant: Intervet Inc., Madison, NJ (US)

(72) Inventors: Dominique Kluger, Klosterneuburg (AT); Albin Hauler, Traiskirchen (AT); Carsten Schmidt, Mainz (DE); David Schroeckenfuchs, Ernstbrunn (AT); Niki Waldron, Vallejo, CA (US)

(73) Assignee: Intervet Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/225,634

(22) Filed: Apr. 8, 2021

(65) Prior Publication Data

US 2021/0236420 A1    Aug. 5, 2021

Related U.S. Application Data

(63) Continuation of application No. 16/515,762, filed on Jul. 18, 2019, now Pat. No. 10,973,759, which is a continuation of application No. 15/988,325, filed on May 24, 2018, now abandoned, which is a continuation of application No. 15/359,917, filed on Nov. 23, 2016, now abandoned, which is a continuation of application No. 14/082,813, filed on Nov. 18, 2013, now Pat. No. 9,532,946.

(60) Provisional application No. 61/791,385, filed on Mar. 15, 2013, provisional application No. 61/728,379, filed on Nov. 20, 2012.

(51) Int. Cl.
| | | |
|---|---|---|
| *A61K 9/00* | (2006.01) | |
| *A61K 47/10* | (2017.01) | |
| *A61K 31/42* | (2006.01) | |
| *B29C 43/00* | (2006.01) | |
| *B29K 71/00* | (2006.01) | |
| *B29K 105/00* | (2006.01) | |
| *B29L 31/00* | (2006.01) | |

(52) U.S. Cl.
CPC ............ *A61K 9/0056* (2013.01); *A61K 31/42* (2013.01); *A61K 47/10* (2013.01); *B29C 43/003* (2013.01); *B29K 2071/02* (2013.01); *B29K 2105/0035* (2013.01); *B29L 2031/753* (2013.01)

(58) Field of Classification Search
None
See application file for complete search history.

(56) References Cited

U.S. PATENT DOCUMENTS

| | | |
|---|---|---|
| 3,006,769 A | 10/1961 | Meulemans |
| 3,486,186 A | 12/1969 | Richards et al. |
| 3,887,964 A | 6/1975 | Richards |
| 3,952,478 A | 4/1976 | Richards et al. |
| 4,054,967 A | 10/1977 | Sandberg et al. |
| 4,059,378 A | 11/1977 | Sollich |
| 4,097,961 A | 7/1978 | Richards |
| 4,182,003 A | 1/1980 | Lamartino et al. |
| 4,334,339 A | 6/1982 | Holly |
| 4,338,702 A | 7/1982 | Holly |
| 4,343,068 A | 8/1982 | Holly |
| 4,356,595 A | 11/1982 | Sandberg et al. |
| 4,372,008 A | 2/1983 | Sandberg |
| 4,535,505 A | 8/1985 | Holly et al. |
| 4,586,888 A | 5/1986 | Anderson |
| 4,597,135 A | 7/1986 | Holly et al. |
| 4,608,731 A | 9/1986 | Holly |
| 4,622,717 A | 11/1986 | Bollinger |
| 4,697,308 A | 10/1987 | Sandberg |
| 4,768,941 A | 9/1988 | Wagner |
| 4,780,931 A | 11/1988 | Powers et al. |
| 4,818,446 A | 4/1989 | Schreiber et al. |
| 4,821,376 A | 4/1989 | Sandberg |
| 4,872,241 A | 10/1989 | Lindee |
| 4,904,495 A | 2/1990 | Spanier |
| 4,975,039 A | 12/1990 | Dare et al. |
| 4,996,743 A | 3/1991 | Janssen |
| 5,000,973 A | 3/1991 | Scaglione et al. |
| 5,021,025 A | 6/1991 | Wagner |
| 5,022,888 A | 6/1991 | Lindee |
| 5,064,584 A | 11/1991 | Jefferies |
| 5,628,993 A | 5/1997 | Yamagata et al. |
| 5,655,436 A | 8/1997 | Soper |
| 5,731,029 A | 3/1998 | Karwowski et al. |
| 5,980,228 A | 11/1999 | Soper |
| 6,112,703 A | 9/2000 | Handelsman |
| 6,217,927 B1 | 4/2001 | Suttle |
| 6,387,381 B2 | 5/2002 | Christensen |

(Continued)

FOREIGN PATENT DOCUMENTS

| | | |
|---|---|---|
| CA | 1047714 A | 2/1979 |
| CN | 1104488 A | 7/1995 |

(Continued)

OTHER PUBLICATIONS

Annexe 2 : Cataloque de la societe Kruger und Salecker disponible en ligne notamment le May 31, 2011. Ce document de 2010 est accessible via l'interface "Wayback Machine" (www.archive.org) en entrant l'adresse suivante: http://www.kands.org/ pdf/KS Catalogue 2010.pdf (60 pages).

(Continued)

*Primary Examiner* — Jennifer A Berrios

(74) *Attorney, Agent, or Firm* — David J. Kerwick

(57) ABSTRACT

A process for the manufacture of semi-plastic pharmaceutical unit doses using a rotary moulding machine and semi-plastic pharmaceutical dosage units obtained by this process.

3 Claims, 6 Drawing Sheets

(56) References Cited

U.S. PATENT DOCUMENTS

| | | |
|---|---|---|
| 6,471,991 B2 | 10/2002 | Robinson et al. |
| 6,685,959 B1 | 2/2004 | Moreau et al. |
| 7,780,987 B2 | 8/2010 | Zhou et al. |
| 8,029,841 B2 | 10/2011 | Van Esbroeck et al. |
| 2003/0082283 A1 | 5/2003 | Capodieci |
| 2003/0170348 A1 | 9/2003 | Mihalos |
| 2006/0141009 A1 | 6/2006 | Huron et al. |
| 2006/0182856 A1 | 8/2006 | Ornelaz |
| 2006/0188622 A1 | 8/2006 | Suttle |
| 2006/0222684 A1 | 10/2006 | Isele |
| 2007/0060494 A1 | 3/2007 | Haldar et al. |
| 2007/0066617 A1 | 3/2007 | Mita et al. |
| 2007/0093416 A1 | 4/2007 | Igarashi et al. |
| 2007/0178204 A1 | 8/2007 | Savul |
| 2008/0075759 A1 | 3/2008 | Paulsen et al. |
| 2008/0138472 A1 | 6/2008 | Alexandre |
| 2009/0280159 A1 | 11/2009 | Paulsen et al. |
| 2011/0027412 A1 | 2/2011 | Spence |
| 2011/0059988 A1 | 3/2011 | Heckeroth |
| 2011/0223234 A1 | 9/2011 | Paulsen et al. |
| 2012/0237662 A1 | 9/2012 | Wang |
| 2013/0259991 A1 | 10/2013 | Lindee et al. |

FOREIGN PATENT DOCUMENTS

| | | |
|---|---|---|
| CN | 1249176 A | 4/2000 |
| CN | 101778566 A | 7/2010 |
| EP | 0107315 A2 | 5/1984 |
| EP | 0387933 A1 | 9/1990 |
| EP | 0743003 A1 | 11/1996 |
| EP | 1163901 A1 | 12/2001 |
| EP | 1808082 A1 | 7/2007 |
| EP | 1695632 B1 | 11/2013 |
| EP | 2833866 B1 | 11/2018 |
| GB | 394489 A | 6/1933 |
| JP | 2006510350 A | 3/2006 |
| JP | 2009120564 A | 6/2009 |
| JP | 2010531883 A | 9/2010 |
| JP | 2010536733 A | 12/2010 |
| JP | 2011503197 A | 1/2011 |
| KR | 20060061923 A | 6/2006 |
| KR | 20090007622 A | 1/2009 |
| NZ | 628144 | 9/2016 |
| NZ | 731588 | 11/2018 |
| RU | 2010109901 A | 9/2011 |
| WO | 2004014143 A1 | 2/2004 |
| WO | 2005013714 A1 | 2/2005 |
| WO | 2005027893 A1 | 3/2005 |
| WO | 2005085216 A1 | 9/2005 |
| WO | 2007067582 A2 | 6/2007 |
| WO | 2007079162 A1 | 7/2007 |
| WO | 2007130478 A2 | 11/2007 |
| WO | 2009002809 A2 | 12/2008 |
| WO | 2009003075 A1 | 12/2008 |
| WO | 2009024541 A2 | 2/2009 |
| WO | 2009064859 A1 | 5/2009 |
| WO | 2009080250 A2 | 7/2009 |
| WO | 2010070068 A2 | 6/2010 |
| WO | 2010079077 A1 | 7/2010 |
| WO | 2011075591 A1 | 6/2011 |
| WO | 2011124998 A1 | 10/2011 |
| WO | 2011149749 A1 | 12/2011 |
| WO | 2012017326 A2 | 2/2012 |
| WO | 2012120154 A2 | 9/2012 |
| WO | 2012120156 A2 | 9/2012 |
| WO | 2013119442 A1 | 8/2013 |
| WO | 2013150052 A1 | 10/2013 |

OTHER PUBLICATIONS

Bravecto, product data sheet dated Jun. 24, 2011, available from: https://www.msdsdigital.com/system/files/Bravecto.pdf, 7 pages.

European Patent Office, Third Party Observation for Application No. EP20130792909, "Manufacturing of semi-plastic pharmaceutical dosage units", Jan. 14, 2021.

European Patent Office, Third party observations for European Patent Application EP20130792909, "Manufacturing of semi-plastic pharmaceutical dosage units", Dec. 23, 2020.

European Patent Office, Translation of Third party observations for European patent application EP20130792909, "Manufacturing of semi-plastic pharmaceutical dosage units", Dec. 23, 2020.

International Search Report for corresponding PCT/EP2013/074127, dated Mar. 28, 2014 (5 pages).

Rohdich, N et al, A randomized, blinded, controlled and multi-centered field study comparing the efficacy and safety of Bravecto™ (fluralaner) against Frontline™ (fipronil) in flea- and tick-infested dogs, Parasites & Vectors, 2014, pp. 1-5, vol. 7, issue 83.

Spectrum PEG 3350 NF MSDS (year 2015)—22 pages.

Arthur H. Kibbe, Editor, Polyethylene Glycol, Handbook of Pharmaceutical Excipients, 2000, 392-398, Third Edition.

Duncan Manley, Editor, Manley's technology of biscuits, crackers and cookies, Woodhead Publishing Series in Food Science, Technology and Nutrition: No. 217, 2011, 454-455, Fourth Edition.

Screenshot confirming the availability of D8 on May 31, 2011 (1 page).

"Pharmacy," Library of Pharmaceutics 1, published on Mar. 2, 2000, see pp. 299 and 300, Fig. 3-4, etc.

Catalogue of the fair interpack 2008 (Messe Dosseldorf GmbH, 2008), interpack mycatalog 2008, Processes and packaging, p. 3377-3378 ("EM390 Rotary Moulder"), 3412-3413 (DFE Meineke Rotary Moulders), obtainable from the internet via https://www.interpack.com/fair/interpack2008/prod-pdf/mycatalog-interpack2008-prod-03- e.pdf, 3 pages.

Confirmation of the public availability of the before-mentioned internet pages via "waybackmachine", screenshots of the capture carried out on Feb. 21, 2011, 3 pages.

Declaration Under 37 C.F.R. § 1.132 of Keith Freehauf, U.S. Appl. No. 14/082,813, dated Jul. 26, 2016, 7 pages.

Declaration Under 37 C.F.R. § 1.132 of Niki Waldron, U.S. Appl. No. 14/082,813, dated Dec. 17, 2015, 8 pages.

European Medicines Agency, Science Medicines Health, CVMP assessment report for Bravecto (EMEA/V/C/002526/0000), Committee for Medicinal Products for Veterinary Use (CVMP), 2013, 22 pages, EMA/18748/2014.

Screenshot of www.medizinfuchs.de concerning bone meal of Canina Pharma GmbH, 1 page.

U.S. Appl. No. 16/515,762, Declaration of Laura Northrup dated Dec. 16, 2020, 8 pages.

Translation of Third Party Observations filed Dec. 17, 2020, 6 pages.

MANUFACTURING OF SEMI-PLASTIC PHARMACEUTICAL DOSAGE UNITS

CROSS-REFERENCE TO RELATED APPLICATIONS

This application is a continuation of U.S. application Ser. No. 16/515,762, filed Jul. 18, 2019, which is a continuation of U.S. application Ser. No. 15/988,325, filed on May 24, 2018, which is a continuation of U.S. application Ser. No. 15/359,917, filed on Nov. 23, 2016, which is a continuation of U.S. application Ser. No. 14/082,813, filed on Nov. 18, 2013, now U.S. Pat. No. 9,532,946, issued Jan. 3, 2017, which claims priority to U.S. Provisional Application No. 61/728,379, filed on Nov. 20, 2012, and 61/791,385, filed on Mar. 15, 2013. The contents of each of these applications are hereby incorporated by reference. No new matter has been added.

FIELD OF THE INVENTION

The invention relates to the field of manufacturing of semi-plastic pharmaceutical dosage units such as soft chews.

BACKGROUND OF THE INVENTION

Chewable pharmaceutical dosage units, such as soft chews, are known and have been commercialized for companion animals. Formulation of a drug into a chewable dosage form can increase (animal) patient acceptance of the medication that tend to resist swallowing hard tablets or capsules and even make the animals take up the dosage form free choice.

Texture is important for the acceptance of such oral dosage units by (animal) patients. One of the most commonly used form for chewable pharmaceutical dosage units is a chewable compressed tablet, whose ingredients, however, can make the tablet gritty or otherwise unappealing, especially to non-human animals. Thus, a preferred alternative dosage form for non-human animals is the "soft chew", generally a meat-like mass also widely found in consumable pet treats.

Soft chewable pharmaceutical dosage units (Soft chews) have been described in the prior art. U.S. Pat. No. 6,387,381 discloses an extrudate which is formed of a matrix having starch, sugar, fat, polyhydric alcohol and water.

WO 2004/014143 relates to compositions and processes for the delivery of an additive to an organism in a form suitable for consumption, and in particular, in the form of a soft chew.

US 2009/0280159 and US 2011/0223234, relate to palatable edible soft chewable medication vehicles. The processes described herein relate to the problem that heat generated during the extrusion process causes deterioration in the stability of the active ingredient in the mixture.

Machines for the production of moulded food patties have been described to be useful for the manufacturing of soft chews for administration to non-human animals. Such machines are moulding machines that have been originally developed for use in producing moulded food products, for example the Formax F6™ moulding machine made by the Formax Corporation or the moulding machines disclosed in U.S. Pat. Nos. 3,486,186; 3,887,964; 3,952,478; 4,054,967; 4,097,961; 4,182,003; 4,334,339; 4,338,702; 4,343,068; 4,356,595; 4,372,008; 4,535,505; 4,597,135; 4,608,731; 4,622,717; 4,697,308; 4,768,941; 4,780,931; 4,818,446; 4,821,376; 4,872,241; 4,975,039; 4,996,743; 5,021,025; 5,022,888; 5,655,436; and 5,980,228.

Such machines are originally used to form e.g. hamburger patties from a supply of ground beef by forcing the ground beef under pressure into a multi-cavity mould plate which is rapidly shuttled on a linear slide between a fill position and a discharge position in which vertically reciprocable knockouts push the patties from the mould cavities. A schematic drawing of such a machine is shown in FIG. 1.

However, it has been observed that with such forming machines there are limitations regarding the size and weight of soft chewable pharmaceutical dosage units that can be produced in the desired quality on large scale.

Accordingly, an alternative process for producing such soft chewable pharmaceutical dosage units and other semi-plastic pharmaceutical dosage units on an industrial scale would be desirable.

Rotary moulding machines are known for the manufacturing of confectionery such as marzipan, fondant, nut compositions, fruit compositions, fudge, caramel, nougat, coconut compositions and the like.

It has now been found that semi-plastic pharmaceutical dosage units, e.g. soft chews, that are formed with a rotary moulding machine have desirable properties and address the problems of the prior art.

SUMMARY OF THE INVENTION

In one aspect the invention is directed to a process for the manufacturing of a semi-plastic pharmaceutical dosage unit, wherein the semi-plastic pharmaceutical dosage unit is formed with a rotary moulding machine.

In one embodiment the process comprises the steps of:
a) mixing at least one active pharmaceutical ingredient with a dry and/or liquid component to prepare a premix,
b) heating a forming agent until melting,
c) mixing the premix and the forming agent together to form a dough,
d) feeding the dough into a container connected with a rotary moulding machine; and
e) forming a semi-plastic pharmaceutical dosage unit in a rotary moulding machine.

In one embodiment the rotary moulding machine comprises forming moulds with concave edges.

In one embodiment the forming agent is polyethylene glycol.

In one embodiment the temperature of the dough in step d) is between 35° C. and 45° C.

In one embodiment the semi-plastic pharmaceutical dosage unit is a soft chewable veterinary pharmaceutical product for oral administration.

In one embodiment the active pharmaceutical ingredient is an isoxazoline compound. In one embodiment the active pharmaceutical ingredient is 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide.

Another aspect of the current invention is a semi-plastic pharmaceutical dosage unit, that is obtainable by such process.

In one embodiment such semi-plastic pharmaceutical dosage unit is a soft chewable veterinary pharmaceutical product for oral administration.

Another aspect of the current invention is a semi-plastic pharmaceutical dosage unit wherein at one end of the three dimensional body the pharmaceutical dosage unit has concave edges.

In one embodiment the semi-plastic pharmaceutical dosage unit is of cylindrical form.

In one embodiment the dosage unit is a soft chewable veterinary pharmaceutical product for oral administration.

In one embodiment the active pharmaceutical ingredient is an isoxazoline compound.

In one embodiment the product comprises as active pharmaceutical ingredient an isoxazoline compound of Formula (I)

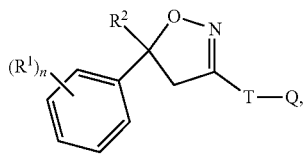

Formula (I)

wherein
$R^1$=halogen, $CF_3$, $OCF_3$, CN,
n=integer from 0 to 3, preferably 1, 2 or 3,
$R^2$=$C_1$-$C_3$-haloalkyl, preferably $CF_3$ or $CF_2Cl$,
T=5- or 6-membered ring, which is optionally substituted by one or more radicals Y,
Y=methyl, halomethyl, halogen, CN, $NO_2$, $NH_2$—C=S, or two adjacent radicals Y form together a chain, especially a three or four membered chain;
Q=X—$NR^3R^4$ or a 5-membered N-heteroaryl ring, which is optionally substituted by one or more radicals;
X=$CH_2$, $CH(CH_3)$, CH(CN), CO, CS,
$R^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methyl-amino, haloethylaminocarbonylmethyl, haloethylaminocarbonylethyl, tetrahydrofuryl, methylaminocarbonylmethyl, (N,N-dimethylamino)carbonylmethyl, propylaminocarbonylmethyl, cyclopropylaminocarbonylmethyl, propenylaminocarbonylmethyl, haloethylaminocarbonylcyclopropyl,

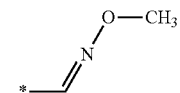

$R^3$-1

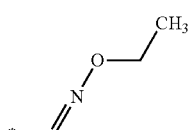

$R^3$-2

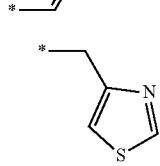

$R^3$-3

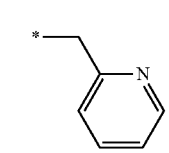

$R^3$-4

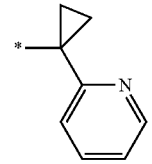

$R^3$-5

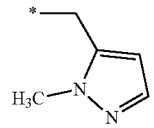

$R^3$-6

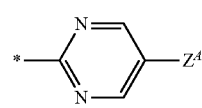

$R^3$-7

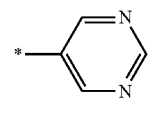

$R^3$-8

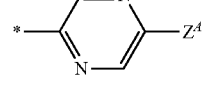

$R^3$-9

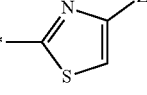

$R^3$-10

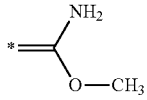

$R^3$-11

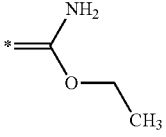

$R^3$-12

$R^3$-13

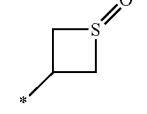

$R^3$-14

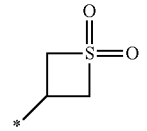

$R^3$-15 wherein $Z^A$=hydrogen, halogen, cyano, halomethyl ($CF_3$);
$R^4$=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl;

Or $R^3$ and $R^4$ together form a substituent selected from the group consisting of:

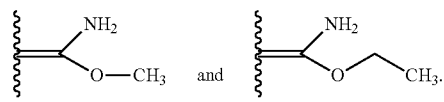

or a salt or solvate thereof.

In a specific embodiment the active pharmaceutical ingredient is 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide.

Another aspect of the current invention is the use of the semi-plastic pharmaceutical dosage unit in the manufacture of a medicament for controlling a parasitic insect, acarid or nematode infestation of an animal.

Another aspect of the current invention is a semi-plastic pharmaceutical dosage unit for the control of parasitic insect, acarida or nematode infestation of an animal.

DETAILED DESCRIPTION OF THE INVENTION

Figure 1:
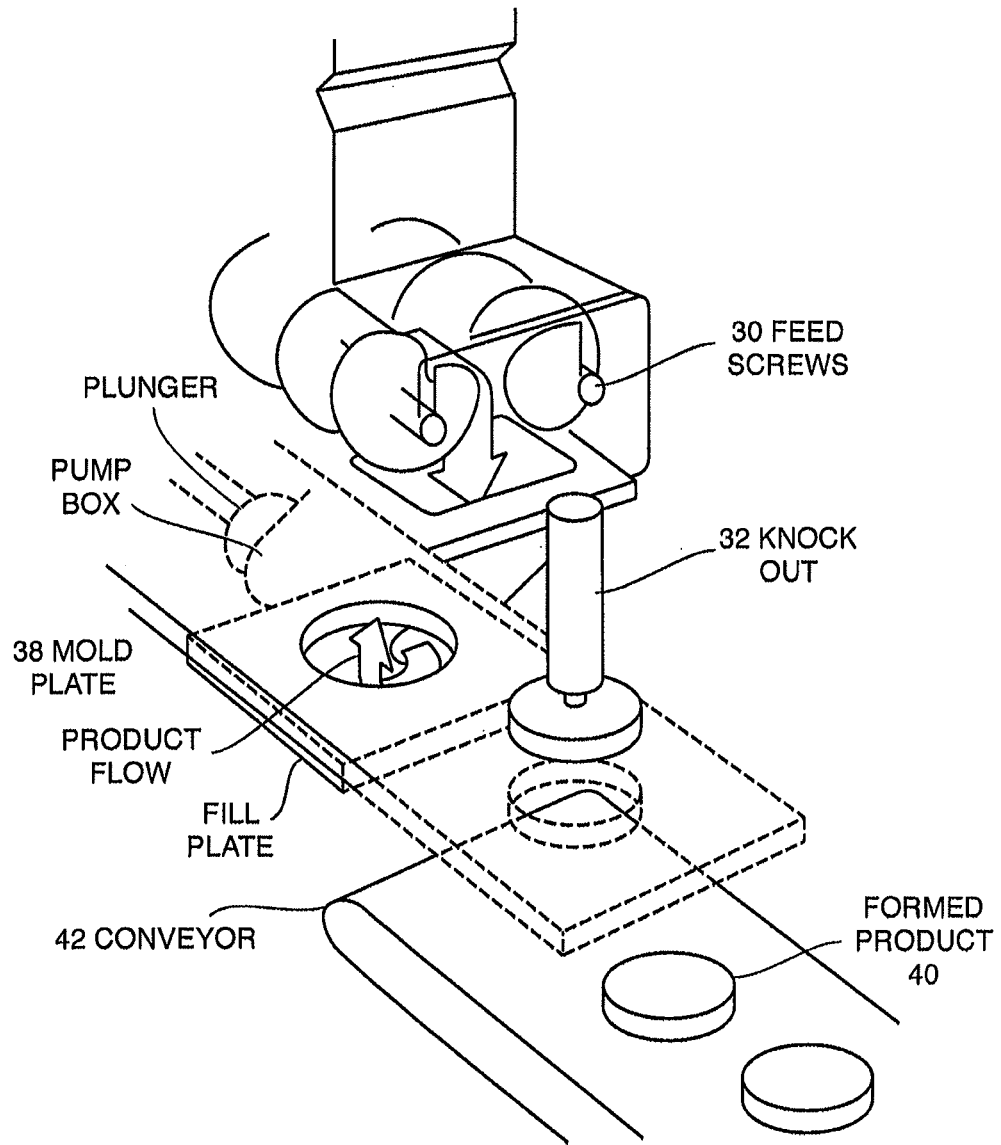
FIG. 1 shows a schema of a knock-out Formax machine

The inventors identified that rotary moulding machines are especially beneficial for the manufacture of soft chews and other semi-plastic pharmaceutical dosage units (products).

For the manufacturing of a semi-plastic pharmaceutical dosage unit on an industrial scale a forming machine is necessary that is able to produce high volume of dosage units with a consistent high quality in order to fulfil pharmaceutical standards. Quality in this regard means, that the dosage units have a weight and size in a specified narrow range, have an uniform appearance (shape) and composition, i.e. they are not broken or deformed and have an smooth surface without cracks. Furthermore it is beneficial that the semi-plastic pharmaceutical dosage units, such as soft chews retain a constant size after the forming process. It has now been found that forming with a rotary moulding machine results in such desirable properties.

Although the process will be described in detail for the manufacturing of soft chewable pharmaceutical dosage units (soft chews), this process can be used analogous to manufacture alternative semi-plastic pharmaceutical dosage units for administration to humans or animals. Examples of contemplated alternative semi-plastic pharmaceutical dosage units are plasters, suppositories for rectal administration or vaginal tablets.

A semi-plastic pharmaceutical dosage unit is a solid (at room temperature) pharmaceutical dosage unit that has a lower hardness and a higher moisture content than a conventional hard tablet. Such dosage unit exhibits a plastic rheological behaviour and can be formed by moulding equipment into many different shapes. In difference to a plastic product, that is three-dimensional, semi-plastic means that the unit dose is a three-dimensional body wherein the bottom of the body is flat. A semi-plastic pharmaceutical dosage unit is after moulding dimensionally stable. The ingredients of such a semi-plastic pharmaceutical dosage unit are of pharmaceutical grade. An illustrative example of a semi-plastic pharmaceutical dosage unit is a soft chew, as described in the prior art and below.

A "Soft chew" or "Soft chewable pharmaceutical product" is intended to mean a pharmaceutical unit dose that is solid at room temperature and that is after oral administration soft to chew by the patient/animal and which is functionally chewy because the product has some plastic texture during the process of mastication in the mouth. Such soft chews have a softness that is similar to a cooked ground meat petty.

It has been now found that with rotary moulding machines a semi-plastic pharmaceutical dosage unit, such as soft chews of different shapes and sizes can be produced in desired quality, that are very difficult or even impossible to be processed on industrial scale on conventional knock-out pressure moulding forming machines that have been described, and are currently used, for the large scale manufacturing of soft chews (e.g. Formax machines).

Especially the industrial processing of small soft chews with the knock-out forming machine e.g. Formax, that have a weight of 2 g or less has been proven to be difficult and did not constantly result in soft chews that are uniform in shape.

Another benefit of rotary moulding machines is the higher yield of the process. i.e. the weight of dosage unit that can be produced from a defined weight of dough that is filled into the machine, the more uniform size and shape of the dosage unit, such as soft chew formed, the possibility of quick cleaning of the moulding machines, and the possibility to change the moulding tools easily.

Rotary moulding machines are known and are generally used in bakery and confectionary food processing. The general concept of rotary moulding machine is that the dough is pressed into a rotating moulder roller (forming roller) and then withdrawn from the moulds without a knockoff or punch mechanism.

One form of a rotary moulding machine comprises two rollers arranged in parallel and in tangential contact with each other, a first roller (A), also referred to as pressure roller, preferably having a grooved surface, and a second roller (B), also referred to as forming roller, having a surface whereon a plurality of forming moulds (or cavities) are arranged according to a set pattern and of dimensions comparable to those of the desired end products. The two rollers are in overhead communication with a hopper (H), wherein previously prepared dough can be loaded. The forming roller moves in opposite angular directions so that the dough is pushed towards the area of tangential contact between the rollers through the grooves of the pressure roller which, still in the above-mentioned contact area, also pushes the dough into the moulds of the forming roller so as to form a dosage unit in each mould.

Figure 2:
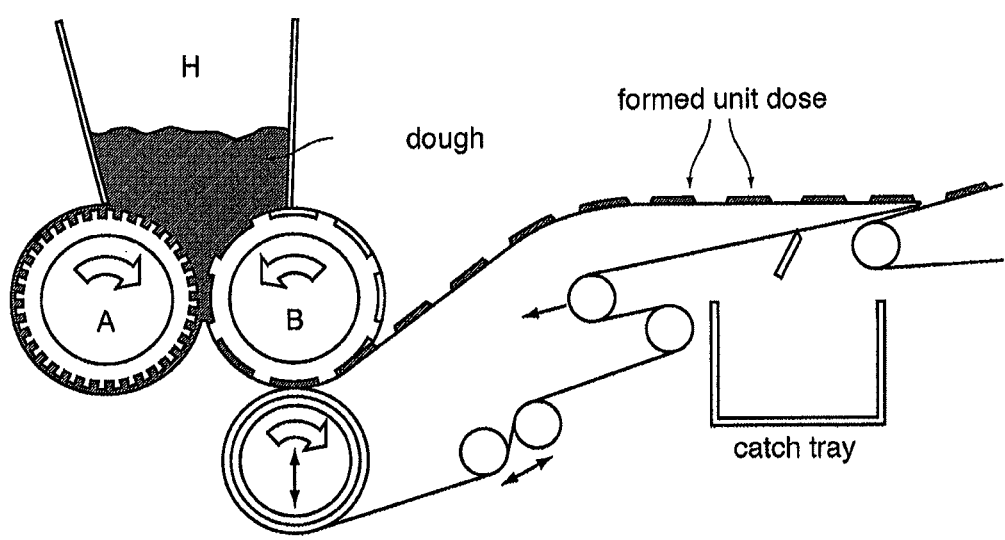
FIG. 2 shows a schema of an example of a rotary moulding machine
Figure 3A:
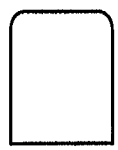
FIGS. 3A-3G show lateral views of examples of soft chews according to the invention that are not capable of being produced by the prior art machine.
Figure 3B:
Figure 3C:
Figure 3D:
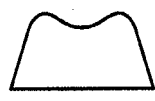
Figure 3E:
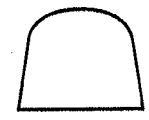
Figure 3F:
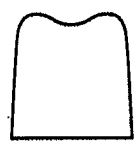
Figure 3G:
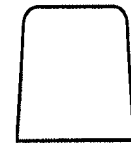
Figure 4:
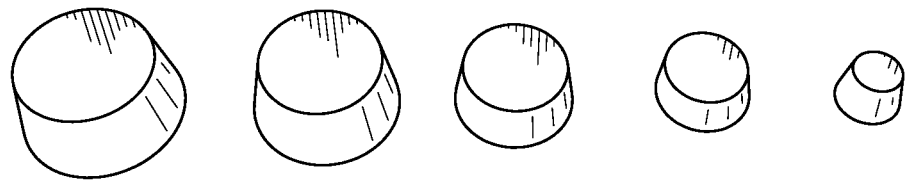
FIGS. 4-6 show semi-plastic pharmaceutical dosage units according to the invention.
Figure 5:
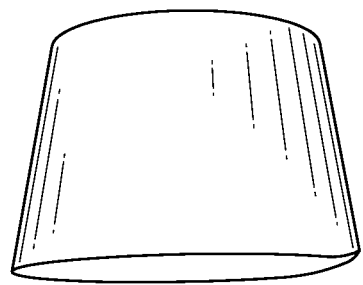
Figure 6:
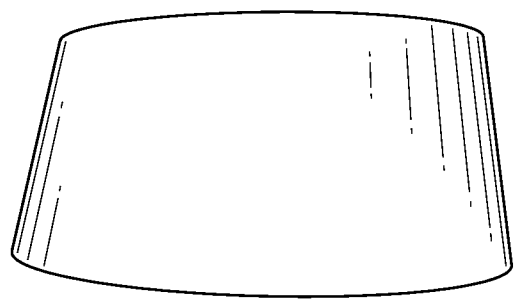

The rotary moulding machine is also equipped with suitable the means to collect the dosage unit from the moulds for then sending them on after drying and hardening to a tray for packaging. A schema of such a rotary moulding machine is shown in FIG. 2.

In an alternative form of a rotary moulder, the hopper of the rotary moulding machine is filled with the dough and by means of a pressure chamber under the hopper the dough is pressed through a nozzle into the rotating moulding roller (forming roller). A suction conveying belt withdraws the pre-moulded product off the forming roller and transports them onwards. At the front of a suction belt there are knife edge and a loosening shaft. Suitable rotary moulding machines for use in the process according to the current invention are e.g. available from Kruger & Salecker Maschinenbau GmbH & Co KG, Bad Schwartau, Germany, (e.g. MFT400) OKA-Spezialmaschinen KG, Darmstadt, Germany or from Sollich KG, Bad Schwartau, Germany.

The dough mass for processing with the rotary moulding machine is in a first step prepared by mixing at least one active pharmaceutical ingredient with a dry and/or liquid component to prepare a premix.

An active pharmaceutical ingredient for use in the process or product according to the current invention (or active ingredient, or pharmaceutically active ingredient or pharmaceutically acceptable active ingredient) is a substance used in a pharmaceutical dosage unit, intended to furnish pharmacological activity or to otherwise have direct effect in the diagnosis, cure, mitigation, treatment or prevention of disease, or to have direct effect in restoring, correcting or modifying physiological functions in humans or animals.

Any pharmaceutically active ingredient may be provided in the process of the invention and in the product according to the invention. Those of ordinary skill in the pharmaceutical arts will be entirely familiar with the identity of such active ingredients which may include, without limitation, antibiotics, analgesics, antivirals, antifungals, antiparasitics such as endo- and ecto-parasiticides, hormones and/or derivatives thereof, anti-inflammatories (including non-steroidal anti-inflammatories), steroids, behavior modifiers, vaccines, antacids, laxatives, anticonvulsants, sedatives, tranquilizers, antitussives, antihistamines, decongestants, expectorants, appetite stimulants and suppressants, cardiovascular drugs, minerals and vitamins.

Useful active pharmaceutical ingredients are preferably antiparasitics, more preferably selected from the group consisting of isoxazoline compounds, avermectins (e.g., ivermectin, selamectin, doramectin, abamectin, and eprinomectin); milbemycins (moxidectin and milbemycin oxime); probenzimidazoles (e.g., febantel, netobimin, and thiophanate); benzimidazole derivatives, such as a thiazole benzimidazole derivatives (e.g., thiabendazole and cambendazole), carbamate benzimidazole derivatives (e.g., fenbendazole, albendazole (oxide), mebendazole, oxfendazole, parbendazole, oxibendazole, flubendazole, and triclabendazole); imidazothiazoles (e.g., levamisole and tetramisole); tetrahydropyrimidine (morantel and pyrantel), salicylanilides (e.g., closantel, oxyclozanide, rafoxanide, and niclosamide); nitrophenolic compounds (e.g., nitroxynil and nitroscanate); benzenedisulfonamides (e.g., clorsulon); pyrazinoisoquinolines (e.g., praziquantel and epsiprantel); heterocyclic compounds (e.g., piperazine, diethylcarbamazine, and phenothiazine); dichlorophen, arsenicals (e.g., thiacetarsamide, melorsamine, and arsenamide); cyclooctadepsipeptides (e.g., emodepside); paraherquamides (e.g. derquantel, amino-acetonitrile compounds (e.g. monepantel, AAD 1566); and amidine compounds (e.g., amidantel and tribendimidin), including all pharmaceutically acceptable forms thereof, such as salts, solvates or N-oxides.

In one embodiment the pharmaceutically active ingredient is an isoxazoline compound. Isoxazoline compounds are known in the art and these compounds and their use as antiparasitic are described, for example, in US patent application US 2007/0066617, and International Patent applications WO 2005/085216, WO 2007/079162, WO 2009/002809, WO 2009/024541, WO 2009/003075, WO 2010/070068 and WO 2010/079077, the disclosures of which, as well as the references cited herein, are incorporated by reference. This class of compounds is known to possess excellent activity against ectoparasites, i.e. parasitic insect and acarids, such as ticks and fleas and endoparasites such as nematodes.

In one embodiment the soft chewable pharmaceutical product according to the invention comprises an isoxazoline compound of the Formula (I)

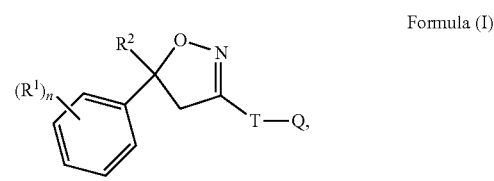

Formula (I)

wherein
R$^1$=halogen, CF$_3$, OCF$_3$, CN,
n=integer from 0 to 3, preferably 1, 2 or 3,
R$^2$=C$_1$-C$_3$-haloalkyl, preferably CF$_3$ or CF$_2$Cl,
T=5- or 6-membered ring, which is optionally substituted by one or more radicals Y,
Y=methyl, halomethyl, halogen, CN, NO$_2$, NH$_2$—C=S, or two adjacent radicals Y form together a chain CH—CH=CH—CH, N—CH=CH—CH, CH—N=CH—CH, CH—CH=N—CH, or CH—CH=CH—N, HC=HC—CH, CH—CH=CH, CH=CH—N, N—CH=CH;
Q=X—NR$^3$R$^4$ or a 5-membered N-heteroaryl ring, which is optionally substituted by one or more radicals Z$^A$, Z$^B$ Z$^D$;
X=CH$_2$, CH(CH$_3$), CH(CN), CO, CS,
R$^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methyl-amino, haloethylaminocarbonylmethyl, haloethylaminocarbonylethyl, tetrahydrofuryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl,

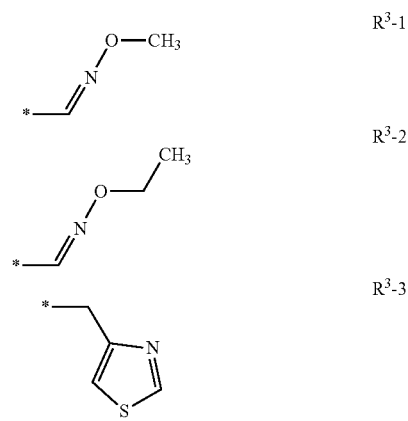

-continued

R³-4 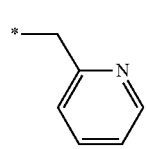

R³-5 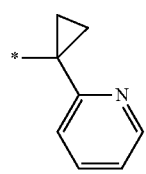

R³-6 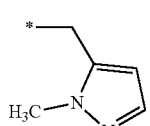

R³-7 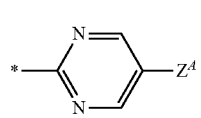

R³-8 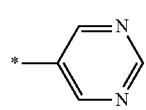

R³-9 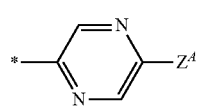

R³-10 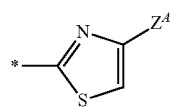

R³-11 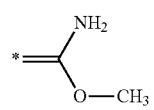

R³-12 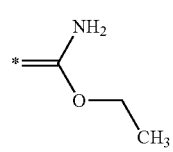

R³-13 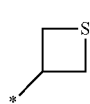

R³-14 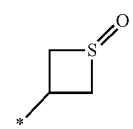

R³-15 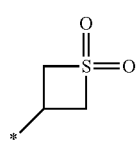

$R^4$=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxyethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl; or $R^3$ and $R^4$ together form a substituent selected from the group consisting of:

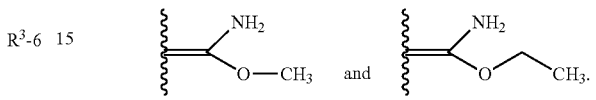

wherein $Z^4$=hydrogen, halogen, cyano, halomethyl ($CF_3$).

In one preferred embodiment in Formula (I) T is selected from

T-1 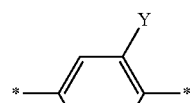

T-2 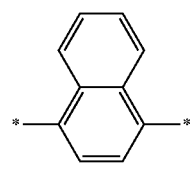

T-3 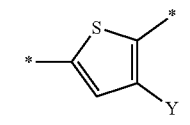

T-4 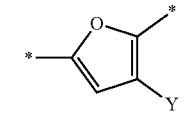

T-5 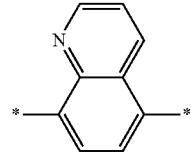

T-6 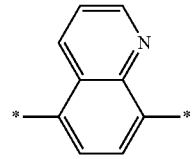

T-7 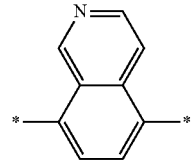

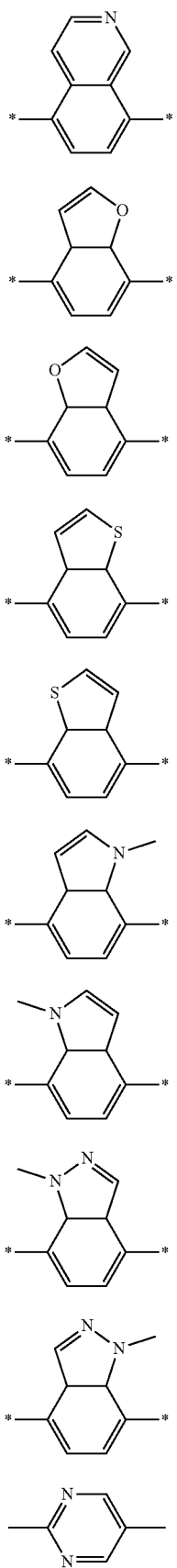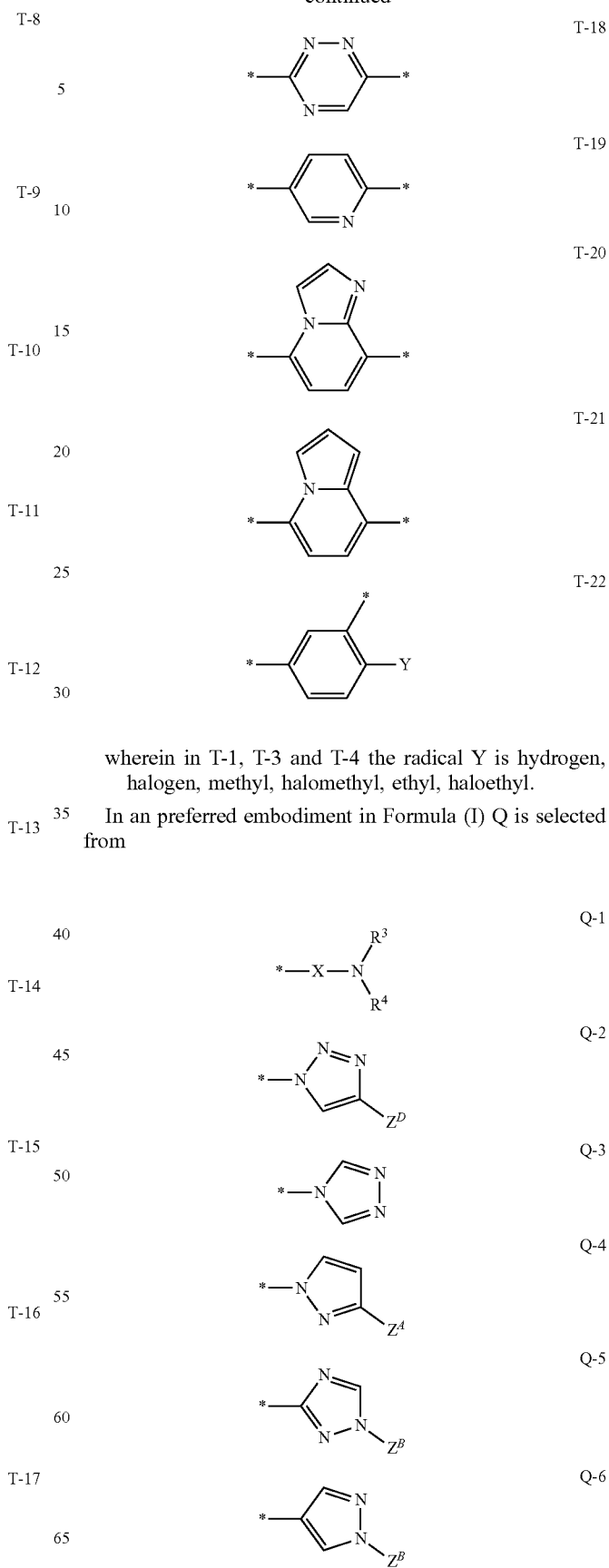
wherein in T-1, T-3 and T-4 the radical Y is hydrogen, halogen, methyl, halomethyl, ethyl, haloethyl.
In an preferred embodiment in Formula (I) Q is selected from -continued Q-7 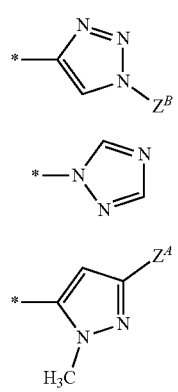

Q-8 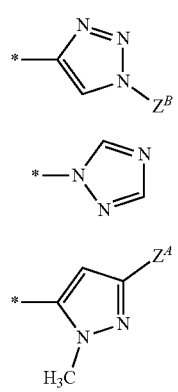

Q-9

Wherein $R^3$, $R^4$, X and $Z^A$ are as defined above.
$Z^B=$ $Z^B$-1

$Z^B$-2

$Z^B$-3

$Z^B$-4

$Z^B$-5

$Z^B$-6

-continued $Z^B$-7 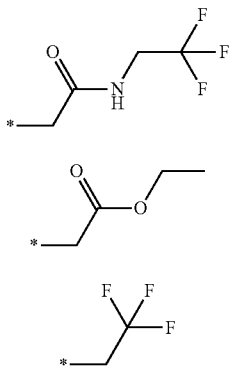

$Z^B$-8 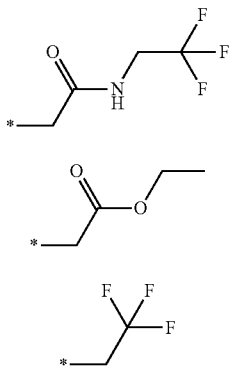

$Z^B$-9 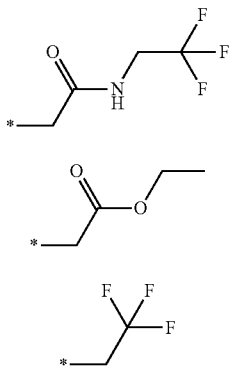

$Z^D=$ $Z^D$-1 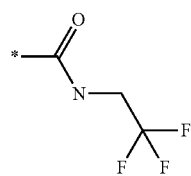

$Z^D$-2 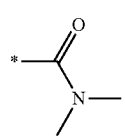

$Z^D$-3 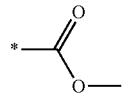

$Z^D$-4 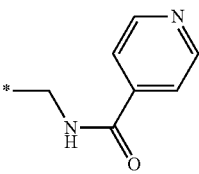

$Z^D$-5 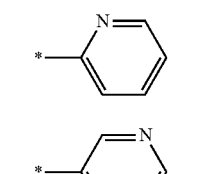

$Z^D$-6 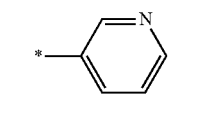

Preferred compounds of Formula (I) are:

| $(R^1)_n$ | $R^2$ | $R^3$ | R4 | T | Y | Q | Z | X |
|---|---|---|---|---|---|---|---|---|
| 3-Cl, 5Cl | $CF_3$ | $CH_2CF_3$ | H | T-2 | — | Q-1 | — | C(O) |
| 3-Cl, 5Cl | $CF_3$ | $CH_2CH_3$ | H | T-2 | — | Q-1 | — | C(O) |
| 3-Cl, 5Cl | $CF_3$ | $CH_2CH_2OCH_3$ | H | T-2 | — | Q-1 | — | C(O) |
| 3-Cl, 5Cl | $CF_3$ | $CH_2C(O)NHCH_2CF_3$ | H | T-2 | — | Q-1 | — | C(O) |
| 3-Cl, 5Cl | $CF_3$ | $CH_2C(O)NHCH_2CH_3$ | H | T-2 | — | Q-1 | — | C(O) |
| 3-$CF_3$, 5-$CF_3$ | $CF_3$ | $CH_2C(O)NHCH_2CF_3$ | H | T-2 | — | Q-1 | — | C(O) |
| 3-$CF_3$, 5-$CF_3$ | $CF_3$ | $CH_2C(O)NHCH_2CH_3$ | H | T-2 | — | Q-1 | — | C(O) |

-continued

| (R¹)ₙ | R² | R³ | R4 | T | Y | Q | Z | X |
|---|---|---|---|---|---|---|---|---|
| 3-CF₃, 5-Cl | CF₃ | CH₂C(O)NHCH₂CF₃ | H | T-2 | — | Q-1 | — | C(O) |
| 3-CF₃, 5-Cl | CF₃ | CH₂C(O)NHCH₂CH₃ | H | T-2 | — | Q-1 | — | C(O) |
| 3-Cl, 5Cl | CF₃ | — | | T-2 | — | Q-6 | Zᴮ-7 | |
| 3-Cl, 5Cl | CF₃ | — | | T-2 | — | Q-7 | Zᴮ-7 | |
| 3-Cl, 5Cl | CF₃ | — | | T-2 | — | Q-5 | Zᴮ-7 | |
| 3-Cl, 5Cl | CF₃ | — | | T-2 | — | Q-2 | Zᴰ-1 | |
| 3-Cl, 5Cl | CF₃ | CH₂C(O)NHCH₂CF₃ | H | T-3 | CH₃ | Q-1 | — | C(O) |
| 3-Cl, 5Cl | CF₃ | CH₂C(O)NHCH₂CC | H | T-3 | CH₃ | Q-1 | — | C(O) |
| 3-Cl, 5Cl | CF₃ | CH₂C(O)NHCH₂CN | H | T-3 | CH₃ | Q-1 | — | C(O) |
| 3-Cl, 5Cl | CF₃ | CH₂C(O)NHCH₂CH₃ | H | T-3 | CH₃ | Q-1 | — | C(O) |
| 3-CF₃, 5-CF₃ | CF₃ | CH₂C(O)NHCH₂CF₃ | H | T-3 | CH₃ | Q-1 | — | C(O) |
| 3-CF₃, 5-CF₃ | CF₃ | CH₂C(O)NHCH₂CH₃ | H | T-3 | CH₃ | Q-1 | — | C(O) |
| 3-Cl, 4-Cl, 5-Cl | CF₃ | CH₂C(O)NHCH₂CF₃ | H | T-3 | CH₃ | Q-1 | — | C(O) |
| 3-Cl, 4-Cl, 5-Cl | CF₃ | CH₂C(O)NHCH₂CH₃ | H | T-3 | CH₃ | Q-1 | — | C(O) |
| 3-Cl, 4-F, 5-Cl | CF₃ | CH₂C(O)NHCH₂CF₃ | H | T-3 | CH₃ | Q-1 | — | C(O) |
| 3-Cl, 4-F, 5-Cl | CF₃ | CH₂C(O)NHCH₂CH₃ | H | T-3 | CH₃ | Q-1 | — | C(O) |
| 3-Cl, 5-Cl | CF₃ | CH₂C(O)NHCH₂CF₃ | H | T-20 | — | Q-1 | — | C(O) |
| 3-Cl, 5-Cl | CF₃ | CH₂C(O)NHCH₂CH₃ | H | T-20 | — | Q-1 | — | C(O) |
| 3-CF₃, 5-CF₃ | CF₃ | CH₂C(O)NHCH₂CF₃ | CH₃ | T-20 | — | Q-1 | — | C(O) |
| 3-CF₃, 5-CF₃ | CF₃ | CH₂C(O)NHCH₂CH₃ | CH₃ | T-20 | — | Q-1 | — | C(O) |
| 3-CF₃, 5-CF₃ | CF₃ | CH₂C(O)NHCH₂CF₃ | H | T-20 | — | Q-1 | — | C(O) |
| 3-CF₃, 5-CF₃ | CF₃ | CH₂C(O)NHCH₂CH₃ | H | T-20 | — | Q-1 | — | C(O) |
| 3-CF₃, 5-CF₃ | CF₃ | CH₂C(O)NHCH₂CF3 | H | T-21 | — | Q-1 | — | C(O) |
| 3-CF₃, 5-CF₃ | CF₃ | CH₂C(O)NHCH₂CH₃ | H | T-21 | — | Q-1 | — | C(O) |
| 3-Cl, 5-Cl | CF₃ | CH₂C(O)NHCH₂CF₃ | H | T-21 | — | Q-1 | — | C(O) |
| 3-Cl, 5-Cl | CF₃ | CH₂C(O)NHCH₂CH₃ | H | T-21 | — | Q-1 | — | C(O) |
| 3-Cl, 5-Cl | CF₃ | CH₂CH₂SCH₃ | H | T-21 | — | Q-1 | — | C(O) |
| 3-Cl, 4-Cl, 5-Cl | CF₃ | C(O)CH₃ | H | T-22 | F | Q-1 | — | CH₂ |
| 3-Cl, 4-Cl, 5-Cl | CF₃ | C(O)CH(CH₃)₂ | H | T-22 | F | Q-1 | — | CH₂ |
| 3-Cl, 4-Cl, 5-Cl | CF₃ | C(O)-cyclo-propyl | H | T-22 | F | Q-1 | — | CH₂ |
| 3-Cl, 4-F, 5-Cl | CF₃ | C(O)CH₃ | H | T-22 | F | Q-1 | — | CH₂ |
| 3-Cl, 4-Cl, 5-Cl | CF₃ | C(O)CH₂CH₃ | H | T-22 | F | Q-1 | — | CH₂ |
| 3-Cl, 4-F, 5-Cl | CF₃ | C(O)CH₃ | H | T-22 | Cl | Q-1 | — | CH₂ |
| 3-Cl, 5-Cl | CF₃ | CH₂C(O)NHCH₂CF₃ | H | T-1 | CH₃ | Q-1 | — | C(O) |
| 3-Cl, 5-Cl | CF₃ | CH₂C(O)NHCH₂CH₃ | H | T-1 | CH₃ | Q-1 | — | C(O) |
| 3-Cl, 5-Cl | CF₃ | R³-1 (Z) | H | T-1 | CH₃ | Q-1 | — | C(O) |
| 3-Cl, 5-Cl | CF₃ | R³-1 (E) | H | T-1 | CH₃ | Q-1 | — | C(O) |

Especially preferred compounds of Formula (I) are

| (R¹)ₙ | R² | R³ | R4 | T | Y | Q | Z | X |
|---|---|---|---|---|---|---|---|---|
| 3-Cl, 5Cl | CF₃ | CH₂CF₃ | H | T-2 | — | Q-1 | — | C(O) |
| 3-Cl, 5Cl | CF₃ | CH₂CH₃ | H | T-2 | — | Q-1 | — | C(O) |
| 3-Cl, 5Cl | CF₃ | CH₂CH₂OCH₃ | H | T-2 | — | Q-1 | — | C(O) |
| 3-Cl, 5Cl | CF₃ | CH₂C(O)NHCH₂CF₃ | H | T-2 | — | Q-1 | — | C(O) |
| 3-CF₃, 5-CF₃ | CF₃ | CH₂C(O)NHCH₂CF₃ | H | | — | Q-1 | — | C(O) |
| 3-CF₃, 5-Cl | CF₃ | CH₂C(O)NHCH₂CF₃ | H | T-2 | — | Q-1 | — | C(O) |
| 3-Cl, 5Cl | CF₃ | — | | T-2 | — | Q-6 | Zᴮ-7 | |
| 3-Cl, 5Cl | CF₃ | — | | T-2 | — | Q-7 | Zᴮ-7 | |
| 3-Cl, 5Cl | CF₃ | — | | T-2 | — | Q-5 | Zᴮ-7 | |
| 3-Cl, 5Cl | CF₃ | — | | T-2 | — | Q-2 | Zᴰ-1 | |
| 3-Cl, 5Cl | CF₃ | CH₂C(O)NHCH₂CF₃ | H | T-3 | CH₃ | Q-1 | — | C(O) |
| 3-Cl, 5Cl | CF₃ | CH₂C(O)NHCH₂CC | H | T-3 | CH₃ | Q-1 | — | C(O) |
| 3-Cl, 5Cl | CF₃ | CH₂C(O)NHCH₂CN | H | T-3 | CH₃ | Q-1 | — | C(O) |
| 3-CF₃, 5-CF₃ | CF₃ | CH₂C(O)NHCH₂CF₃ | H | T-3 | CH₃ | Q-1 | — | C(O) |
| 3-Cl, 4-Cl, 5-Cl | CF₃ | CH₂C(O)NHCH₂CF₃ | H | T-3 | CH₃ | Q-1 | — | C(O) |
| 3-Cl, 4-F, 5-Cl | CF₃ | CH₂C(O)NHCH₂CF₃ | H | T-3 | CH₃ | Q-1 | — | C(O) |
| 3-Cl, 5-Cl | CF₃ | CH₂C(O)NHCH₂CF₃ | H | T-20 | — | Q-1 | — | C(O) |
| 3-CF₃, 5-CF₃ | CF₃ | CH₂C(O)NHCH₂CF₃ | CH₃ | T-20 | — | Q-1 | — | C(O) |
| 3-CF₃, 5-CF₃ | CF₃ | CH₂C(O)NHCH₂CF₃ | H | T-20 | — | Q-1 | — | C(O) |
| 3-CF₃, 5-CF₃ | CF₃ | CH₂C(O)NHCH₂CF₃ | H | T-21 | — | Q-1 | — | C(O) |
| 3-Cl, 5-Cl | CF₃ | CH₂C(O)NHCH₂CF₃ | H | T-21 | — | Q-1 | — | C(O) |
| 3-Cl, 5-Cl | CF₃ | CH₂CH₂SCH₃ | H | T-21 | — | Q-1 | — | C(O) |
| 3-Cl, 4-Cl, 5-Cl | CF₃ | C(O)CH₃ | H | T-22 | F | Q-1 | — | CH₂ |
| 3-Cl, 4-Cl, 5-Cl | CF₃ | C(O)CH(CH₃)₂ | H | T-22 | F | Q-1 | — | CH₂ |
| 3-Cl, 4-Cl, 5-Cl | CF₃ | C(O)-cyclo-propyl | H | T-22 | F | Q-1 | — | CH₂ |
| 3-Cl, 4-F, 5-Cl | CF₃ | C(O)CH₃ | H | T-22 | F | Q-1 | — | CH₂ |
| 3-Cl, 4-Cl, 5-Cl | CF₃ | C(O)CH₂CH₃ | H | T-22 | F | Q-1 | — | CH₂ |
| 3-Cl, 4-F, 5-Cl | CF₃ | C(O)CH₃ | H | T-22 | Cl | Q-1 | — | CH₂ |
| 3-Cl, 5-Cl | CF₃ | CH₂C(O)NHCH₂CF₃ | H | T-1 | CH₃ | Q-1 | — | C(O) |
| 3-Cl, 5-Cl | CF₃ | R³-1 (Z) | H | T-1 | CH₃ | Q-1 | — | C(O) |
| 3-Cl, 5-Cl | CF₃ | R³-1 (E) | H | T-1 | CH₃ | Q-1 | — | C(O) |

A more preferred compound has the Formula (II),

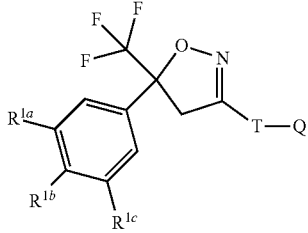

Formula II wherein $R^{1a}$, $R^{1b}$, $R^{1c}$ are independently from each other hydrogen, Cl or $CF_3$, preferably $R^{1a}$ and $R^{1c}$ are Cl or $CF_3$ and Rib is hydrogen, T is T-1
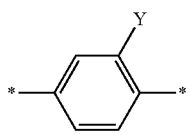

T-2
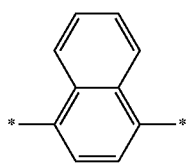

T-3
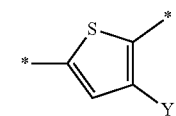

T-20
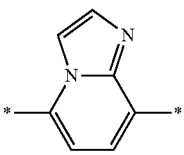

T-21
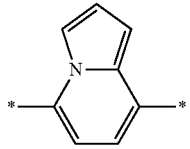

wherein Y is methyl, bromine, Cl, F, CN or $C(S)NH_2$, and Q is as described above.

In another preferred embodiment in $R^3$ is H and $R^4$ is —$CH_2$—C(O)—NH—$CH_2$—$CF_3$, —$CH_2$—C(O)—NH—$CH_2$—$CH_3$, —$CH_2$—$CH_2$—$CF_3$ or —$CH_2$—$CF_3$.

In one embodiment the compound of Formula (I) is 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide (CAS RN 864731-61-3—USAN fluralaner).

In another embodiment the compound of Formula (I) is (Z)-4-[5-(3,5-Dichlorophenyl)-5-trifluoromethyl-4,5-dihydroisoxazol-3-yl]-N-[(methoxyimino)methyl]-2-methylbenzamide (CAS RN 928789-76-8).

In another embodiment the compound of Formula (I) is 4-[5-(3,5-dichlorophenyl)-5-(trifluoromethyl)-4H-isoxazol-3-yl]-2-methyl-N-(thietan-3-yl)benzamide (CAS RN 1164267-94-0) that was disclosed in WO2009/0080250.

In another embodiment the compound of Formula (I) is 4-[5-[3-Chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide (CAS RN 1093861-60-9, USAN—afoxolaner) that was disclosed in WO2007/079162-.

In another embodiment the compound of Formula (I) is 5-[5-(3,5-Dichlorophenyl)-4,5-dihydro-5-(trifluoromethyl)-3-isoxazolyl]-3-methyl-N-[2-oxo-2-[(2,2,2-trifluoroethyl)amino]ethyl]-2-thiophenecarboxamide (CAS RN 1231754-09-8) that was disclosed in WO2010/070068.

An especially preferred compound is

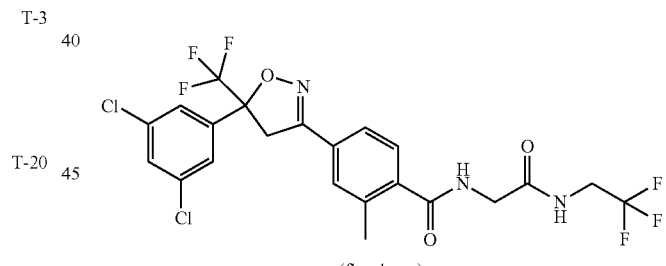

(fluralaner)

Especially preferred compounds of Formula (II) are:

| $(R^1)_n$ | $R^2$ | $R^3$ | R4 | T | Y | Q | Z | X |
|---|---|---|---|---|---|---|---|---|
| 3-Cl, 5Cl | $CF_3$ | $CH_2CF_3$ | H | T-2 | — | Q-1 | — | C(O) |
| 3-Cl, 5Cl | $CF_3$ | $CH_2C(O)NHCH_2CF_3$ | H | T-2 | — | Q-1 | — | C(O) |
| 3-$CF_3$, 5-$CF_3$ | $CF_3$ | $CH_2C(O)NHCH_2CF_3$ | H | T-2 | — | Q-1 | — | C(O) |
| 3-$CF_3$, 5-Cl | $CF_3$ | $CH_2C(O)NHCH_2CF_3$ | H | T-2 | — | Q-1 | — | C(O) |
| 3-Cl, 5Cl | $CF_3$ | — | | T-2 | — | Q-6 | $Z^B$-7 | |
| 3-Cl, 5Cl | $CF_3$ | — | — | T-2 | — | Q-7 | $Z^B$-7 | |
| 3-Cl, 5Cl | $CF_3$ | — | — | T-2 | — | Q-5 | $Z^B$-7 | |
| 3-Cl, 5Cl | $CF_3$ | — | — | T-2 | — | Q-2 | $Z^D$-1 | |
| 3-Cl, 5Cl | $CF_3$ | $CH_2C(O)NHCH_2CF_3$ | H | T-3 | $CH_3$ | Q-1 | — | C(O) |
| 3-$CF_3$, 5-$CF_3$ | $CF_3$ | $CH_2C(O)NHCH_2CF_3$ | H | T-3 | $CH_3$ | Q-1 | — | C(O) |
| 3-Cl, 4-Cl, 5-Cl | $CF_3$ | $CH_2C(O)NHCH_2CF_3$ | H | T-3 | $CH_3$ | Q-1 | — | C(O) |
| 3-Cl, 4-F, 5-Cl | $CF_3$ | $CH2C(O)NHCH_2CF_3$ | H | T-3 | $CH_3$ | Q-1 | — | C(O) |

-continued

| $(R^1)_n$ | $R^2$ | $R^3$ | R4 | T | Y | Q | Z | X |
|---|---|---|---|---|---|---|---|---|
| 3-Cl, 5-Cl | $CF_3$ | CH2C(O)NHCH$_2$CF$_3$ | H | T-20 | — | Q-1 | — | C(O) |
| 3-CF$_3$, 5-CF$_3$ | $CF_3$ | CH$_2$C(O)NHCH$_2$CF3 | CH$_3$ | T-20 | — | Q-1 | — | C(O) |
| 3-CF$_3$, 5-CF$_3$ | $CF_3$ | CH$_2$C(O)NHCH$_2$CF3 | H | T-20 | — | Q-1 | — | C(O) |
| 3-CF$_3$, 5-CF$_3$ | $CF_3$ | CH$_2$C(O)NHCH$_2$CF3 | H | T-21 | — | Q-1 | — | C(O) |
| 3-Cl, 5-Cl | $CF_3$ | CH$_2$C(O)NHCH$_2$CF3 | H | T-21 | — | Q-1 | — | C(O) |
| 3-Cl, 5-Cl | $CF_3$ | CH$_2$C(O)NHCH$_2$CF3 | H | T-1 | CH$_3$ | Q-1 | — | C(O) |
| 3-Cl, 5-Cl | $CF_3$ | $R^3$-1 (Z) | H | T-1 | CH$_3$ | Q-1 | — | C(O) |
| 3-Cl, 5-Cl | $CF_3$ | $R^3$-1 (E) | H | T-1 | CH$_3$ | Q-1 | — | C(O) |

Isoxazoline compounds are known in the art and these compounds and their use as parasiticide are described, for example, in US patent application No. US 2007/0066617, and International Patent applications WO 2007/079162, WO 2009/002809, WO 2009/024541, WO 2009/003075, WO2009/080250, WO 2010/070068, WO 2010/079077, WO 2011/075591 and WO 2011/124998, the disclosures of which, as well as the references cited herein, are incorporated by reference. This class of compounds is known to possess excellent activity against ectoparasites such as ticks and fleas.

The isoxazoline compounds may exist in various isomeric forms. A reference to an isoxazoline compound always includes all possible isomeric forms of such compound. Unless otherwise stated, a compound structure that does not indicate a particular conformation is intended to encompass compositions of all the possible conformational isomers of the compound, as well as compositions comprising fewer than all the possible conformational isomers. In some embodiments, the compound is a chiral compound. In some embodiments, the compound is a non-chiral compound.

Isoxazoline compounds of Formula (I) can be prepared according to one or other of the processes described e.g. in Patent Applications US 2007/0066617, WO 2007/079162, WO 2009/002809, WO 2009/080250, WO 2010/070068, WO 2010/079077, 2011/075591 and WO 2011/124998 or any other process coming within the competence of a person skilled in the art who is an expert in chemical synthesis. For the chemical preparation of the products of the invention, a person skilled in the art is regarded as having at his disposal, inter alia, the entire contents of "Chemical Abstracts" and of the documents which are cited therein.

In one embodiment the isoxazoline compound is 4-[5-(3, 5-Dichlorophenyl)-5-trifluoromethyl-4,5-dihydroisoxazol-3-yl]-2-methyl-N-[(2,2,2-trifluoro-ethylcarbamoyl)-methyl]-benzamide (CAS RN [864731-61-3])—USAN furalaner—Compound A.

The active pharmaceutical ingredient can also comprise combinations of more than one pharmaceutically active ingredient. Preferred combinations comprise active pharmaceutical ingredients selected from the group consisting of isoxazolines with avermectins or milbemycins. In one embodiment the soft chew comprises a combination of isoxazolines, especially fluralaner—compound A or afoxolaner, with ivermectin. In another embodiment the soft chew comprises a combination of isoxazolines, especially fluralaner-compound A or afoxolaner, with milbemycin or moxidectin.

Other combinations of the present invention can include insect or acarid growth regulators (AGRs or IGRs) such as e.g. fenoxycarb, lufenuron, diflubenzuron, novaluron, triflumuron, fluazuron, cyromazine, methoprene, pyriproxyfen etc., thereby providing both initial and sustained control of parasites (at all stages of insect development, including eggs) on the animal subject, as well as within the environment of the animal subject.

The dry components are solid excipients that are generally provided as powders or granules. Dry components conventionally used in pharmaceutical compositions that can be present in the soft chew are e.g. filler(s), flavour(s), and/or sugar components.

As used herein, the term "filler" or "filler component" means and refers to those food-stuffs containing a preponderance of starch and/or starch-like material. Examples of filler are cereal grains and meals or flours obtained upon grinding cereal grains such as corn, oats, wheat, milo, barley, rice, and the various milling by-products of these cereal grains such as wheat feed flour, wheat middlings, mixed feed, wheat shorts, wheat red dog, oat, hominy feed, and other such material. Alternative non-food stuff fillers such as e.g. lactose may be used. In one embodiment the filler is starch, corn starch being preferred.

Flavours are commonly added to soft chewable pharmaceutical products to enhance their palatability. For example, a veterinary medication might include animal product-based flavourings such as beef, pork, chicken, turkey, fish and lamb, liver, milk, cheese and egg may be utilized. Non-animal origin flavourings are plant proteins, such as soy protein, yeasts, or lactose to which edible artificial food-like flavourings has been added. Depending on the target animal, other non-animal flavourings could include anise oil, carob, peanuts, fruit flavours, herbs such as parsley, celery leaves, peppermint, spearmint, garlic, or combinations thereof.

The sugar component may act as a sweetener, filler or flavour or provides a texture that is appealing to the animal, e.g. crunchy texture. As used herein, the term "sugar component" and any conjugation thereof, means and refers to any saccharide which is at least partially soluble in moisture, non-toxic, and preferably not provide any undesirable taste effects. Further, the use of the term "sugar" shall include a "sugar substitute" or an "artificial sweetener". The sugar component may comprise white sugar, corn syrup, sorbitol, mannitol, oligosaccharide, isomalto oligosaccharide, fructose, lactose, glucose, lycasin, xylitol, lactitol, erythritol, mannitol, isomaltose, polydextrose, raffinose, dextrin, galactose, sucrose, invert sugar, honey, molasses, polyhydric alcohols and other similar saccharides oligomers and polymers and mixture thereof or artificial sweeteners such as saccharine, aspartame and other dipeptide sweeteners. In one embodiment the sweetener is aspartame.

Various embodiments further comprise additional excipients such as surfactants, stabilizer, flow agents, disintegration agents, preservatives and/or lubricating agents.

Surfactant components are well-known in the art. A suitable surfactant is e.g. sodium lauryl sulphate.

Suitable stabilizer components are citric acid, sodium citrate, and/or the like and antioxidants such as BHT, BHA, Ascorbic acid, Tocopherol, EDTA.

Flow agents typically may include silica dioxide, modified silica, fumed silica, talc and any other suitable material to assist bulk movement of active components and/or the combination during delivery and/or manufacture.

Disintegration agents typically may include sodium starch glycolate, pregelatinized corn starch (Starch 1500), crospovidone (Polyplasdone XL™, International Specialty Products), and croscarmellose sodium (Ac-Di-Sol™, FMC Corp.), and derivatives thereof and any other suitable material to help breakdown the dosage form and to assist in delivery of active ingredients.

Preservative for oral formulations are known in the art and are included in order to retard growth of microorganisms such as bacteria and fungi. An embodiment of preservative includes products such as potassium sorbate, sodium benzoate or calcium propionate.

Lubricating agents are e.g. magnesium stearate, fumaric acid, sodium stearyl fumarate and sodium pamoate.

Liquid components of pharmaceutical compositions are known to the skilled person. The liquid components are in general aqueous and non-aqueous liquids or mixtures of such liquids.

In one embodiment of the process the liquid component comprises an oil, or a mixture of oils. In another embodiment the liquid component comprises one or more oils and one or more non-aqueous solvents. In one embodiment the liquid component comprises one or more oils, one or more non-aqueous solvents and a humectant.

The oil employed in the soft chew may be a saturated or unsaturated liquid fatty acid, its glyceride derivatives or fatty acid derivatives of plant or animal origin or a mixture thereof. Suitable sources for vegetable fats or oils can be palm oil, corn oil, castor oil, canola oil safflower oil, cotton-seed oil, soybean oil, olive oil, peanut oil and mixtures thereof. Additionally, animal oil or fats and a mixture of animal or vegetable oils or fats are suitable for use in the dosage unit according to the invention. Vegetable oils may also be utilized to lubricate the soft chew mixture and maintain its softness. In one embodiment the oily component is soybean oil.

As used herein, the term "non-aqueous solvent" is intended to mean any liquid other than water in which a biological material may be dissolved or suspended and includes both inorganic solvents and, more preferably, organic solvents.

Illustrative examples of suitable non-aqueous solvents include, but are not limited to, the following: acetone, acetonitrile, benzyl alcohol, butyl diglycol, dimethylacetamide (DMA), dimethylsulfoxide (DMSO), dimethylformamide, N,N-diethyl-3-methylbenzamide, dipropylene glycol n-butyl ether, ethyl alcohol, isopropanol, methanol, butanol, phenylethyl alcohol, isopropanol, ethylene glycol monoethyl ether, ethylene glycol monomethyl ether, monomethylaceamide, dipropylene glycol monomethyl ether, liquid polyoxyethylene glycols, propylene glycol, N-methylpyrrolidone, 2-pyrrolidone, diethylene glycol monoethyl ether, ethylene glycol, diethyl phthalate, polyethoxylated castor oil, methyl ethyl ketone, ethyl-L-lactate, lactic acid, fructone, glycerol formal, ethyl acetate, 1-methoxy-2-propyl acetate, ethyl acetoacetate, geranyl acetate, benzyl benzoate, propylene carbonate, methyl salicylate, isopropylidene glycerol, propylene glycol methyl ether, diethylene glycol monoethyl ether.

As used herein, the term "humectant" means and refers to a hygroscopic substance. It can be a molecule with several hydrophilic groups, e.g. hydroxyl groups, but amines and carboxyl groups, sometimes esterified, can be encountered as well, the affinity to form hydrogen bonds with molecules of water is crucial here.

The humectant has the effect of keeping the soft chew dough moist. Examples of humectants include propylene glycol, glyceryl triacetate, vinyl alcohol and neoagarobiose. Others can be sugar polyols such as glycerol, sorbitol, xylitol and maltitol, polymeric polyols like polydextrose, or natural extracts like quillaia, lactic acid, or urea. In one embodiment the humectant is glycerol.

In an embodiment, the liquid component comprises about 5% to about 50% w/w of the soft chew. In an alternate embodiment, a liquid component comprises about 7.5% to about 40% w/w of the soft chew. In an alternate embodiment, a liquid component comprises about 10% to about 30% w/w of the soft chew. In an alternate embodiment, a liquid component comprises about 15% to about 25% w/w of the soft chew.

The dry and liquid components to be used in the process according to the current invention conventionally further comprise physiologically acceptable formulation excipients known in the art e.g. as described in "Gennaro, Remington: The Science and Practice of Pharmacy" (20th Edition, 2000) incorporated by reference herein. All such ingredients, carriers and excipients must be substantially pharmaceutically or veterinary pure and non-toxic in the amounts employed and must be compatible with the pharmaceutically active ingredients.

The dry ingredients and liquid ingredients are mixed by conventional equipment until the homogeneous blending to form a premix. The skilled person is aware of suitable blending equipment, e.g. a ploughshare mixing blender. In a second step the forming agent is heated until melting.

The forming agent is an excipient that is solid at room temperature and has a melting point between 45 and 100° C. It is included in the composition in molten form and is important for the texture of the soft chew and the possibility to form single soft chews from the dough that stay intact and separate. At ambient temperature the forming agent solidifies and leads to dimensionable stable dosage units after hardening. A suitable forming agent is for example wax or a polymer e.g. polyethylene glycol (PEG) or polyvinylpyrrolidone (PVP).

In an embodiment, a forming agent of choice is polyethylene glycol (PEG). Moreover, depending upon the desired consistency of the soft chew, different molecular weight PEG may be utilized. In an embodiment, PEG 3350 is utilized. However, the molecular weight may be higher or lower than 3350, but preferably higher than 600. Alternatively PEG 8000 might be used.

In an embodiment, the forming agent comprises about 1% to about 40% w/w of the soft chew. In an alternate embodiment, a forming agent comprises about 5% to about 30% w/w % of the soft chew. In an alternate embodiment, a forming agent comprises about 10% to about 20% w/w of the soft chew. In case the forming agent is polyvinylpyrrolidone e.g. 2, 4, 5, 6 or 9% w/w are present in the soft chew.

In a third step the premix that is formed by mixing the active pharmaceutical ingredient and the dry and liquid components as described above and the molten forming agent are mixed to form the dough for processing in the rotary moulding machine.

Conventional equipment can be used for this step. After the forming agent and the premix are homogeneously mixed to form a mouldable dough (a soft, pliable mass that comprises the active pharmaceutical ingredient, the dry and liquid components and the forming agent), the dough is fed into a container (e.g. hopper) connected with a rotary moulding machine. Alternatively the container can be an alternate means to transport dough to the forming roll of the rotary moulding machine e.g. a screw conveyor.

The temperature of the dough is important for the processing in the rotary moulding machine. Preferably the dough has at the time it is filled into the hopper of the rotary moulding machine a temperature between about 35° C. and about 45° C. In another embodiment the temperature of the dough is between about 37° and about 43° C. In another embodiment the temperature of the dough is between about 42° and about 45° C.

Preferably the temperature of the dough can be controlled during the mixing step of the premix and the forming agent, during the transport to the forming roll of the rotary moulding machine and/or during the forming process in the rotary moulding machine. In one embodiment in the process of the current invention in the rotary moulding machine the temperature of the hopper is controlled, e.g. by a jacket comprising a liquid that controls the temperature, typically between about 35° to about 45° C.

In another embodiment, additionally or independently, the temperature of the forming roller of the rotary moulding machine is controlled, preferably cooled e.g. by means of a jacked with temperature controlled liquid. Alternative means to control the temperature of such equipment are known to the skilled person.

The dough is then processed in a rotary moulding machine to form semi-plastic pharmaceutical unit doses.

The process of the invention can be conducted on a continuous or batch basis.

The roller(s) of the rotary moulding machine to be used in the process according to the current invention can be made of plastics or metal. In one embodiment the forming roll is in the form of a mono block and the forming moulds are engraved in a mono block.

In one embodiment the forming roll is made of stainless steel and the forming moulds can be equipped with plastic inlays with or without coating. In one embodiment the forming roller comprises forming moulds with concave edges.

To ensure that the dough like mass is able to come out of the forming mould several different technical options are available. The mass can be sucked out of the forming mould with a rough conveyor belt or with a conveyor belt with vacuum suction.

In one embodiment the conveyor belt is made of a material having an adhesion coefficient towards the dough higher than that of the material of the forming roller. Thanks to this adhesion difference, the conveyor belt can extract and collect on its conveying surface the dosage unit from the moulds which cross the portion of the conveyor belt in contact with the forming roller. In case such a suction conveyor belt is used, the forming roll can be one roll wherein the forming moulds are in a mono block and no additional devices to support the de-moulding of the soft chews are employed.

Another option might be using air pressured which pushes the mass out of the forming mould. One technical solution to remove the moulded dosage unit from the forming mould by pressurized gas is described in U.S. Pat. No. 8,029,841 incorporated by reference herein.

Each batch of dosage units (e.g. soft chew) may be packaged in bulk or, preferably, each soft chew is then individually packaged for storage and distribution. Examples of suitable packaging materials include HDPE bottles, blister or foil/foil packaging.

Blisters are useful for individual packaging of dosage units such as soft chews. For such blister packaging it is important that the dosage units such as soft chews have consistent dimensions and do not change their dimensions after the forming process and have a consistent shape in order to avoid a high percentage of out-layers. Furthermore it is beneficial that the dosage units such as soft chews stay intact and do not break in case the packaging undergoes physical stress during g transport, storage or handling.

Another aspect of the current invention is a semi-plastic pharmaceutical dosage unit obtainable by the process described above. The dosage units, especially soft chewable pharmaceutical products (e.g. soft chews) that are obtainable by such process have a consistent micro consistence and do not show a dilatation (i.e. do not expand) after forming. Such dosage units have a homogeneous structure within the individual soft chew and the active pharmaceutical ingredient and the dry and liquid components are distributed evenly throughout the dosage unit.

Such dosage units can have different weights and dimensions that can be adapted to the weight of the target animal or patient to be treated and the active pharmaceutical ingredient that will be administered in order to allow accurate dosing.

In one embodiment the dosage unit (e.g. soft chew) has a weight between 0.5 and 50 g.

In one embodiment the dosage unit has a weight between 0.7 and 12 g. In one embodiment the dosage unit has a weight of about 2 g and less. In another embodiment the weight of the dosage unit of about 1.5 g or less, in another embodiment the weight of the dosage unit is about 1 g or less. In another embodiment the weight of the dosage unit is about 0.5 g, about 0.6 g, about 0.8 g, about 0.9 g, about 1.1 g, about 1.2 g, about 1.3 g, about 1.4 g, about 1.6 g, or about 1.7 g, about 1.8 g.

In another embodiment the dosage unit (e.g. soft chew) has a weight of more than about 4 g. In one embodiment the dosage unit has a weight more than about 7 g. In another embodiment the weight of the dosage unit is more than about 10 g. In another embodiment the weight of the dosage unit is about 4 g, about 5 g, about 6 g, about 7 g, about 8 g, about 9 g, about 10 g, about 11 g, about 12 g, about 13, g, about 14. g, or about 15 g.

The semi-plastic pharmaceutical dosage units (e.g. soft chews) are of a three-dimensional body with a plan (flat) surface at the bottom (semi-plastic pharmaceutical dosage unit). The edges between the lateral surface and the bottom surface have a sharp angle between 45° and 110°. In one embodiment the sharp angle of the lateral surface and the bottom surface is about 90°. The angle of the edges of the lateral surface is not necessarily equal at all points of the bottom surface.

At the other end of the body (the top surface) the semi-plastic pharmaceutical dosage unit (e.g. soft chew) has at least one concave, rounded edge. The rounded edge of the dosage unit decrease the risk that the dosage unit is deformed and limit the risk that pieces of the dosage unit break away if the unit dosage during packaging or handling is exposed to physical stress. In case pieces of the dosage unit are separated the patient or animal would not receive the full dosage of the active pharmaceutical ingredient after administration of the dosage unit.

The top surface of the semi-plastic pharmaceutical dosage unit (e.g. soft chew) has a plan (flat), concave or convex regular or irregular surface, optionally with imprints. In one embodiment the dosage unit has a concave top surface.

The top and/or the bottom surface of a dosage unit can have in general any shape. The shape of the dosage unit can be adapted to facilitate the administration to the patient/target animal or, especially in case of animal patients, supports the voluntary intake of the soft chew. In one embodiment the top and/or bottom surfaces of the dosage unit, especially soft chew are in the shape that is generally used for an animal treat, e.g. in the form of a star, a cross, a triangle or a bone. Alternatively the top and/or bottom surface of a dosage unit are cylindroid, e.g. elliptic or circular or rectangular. In one embodiment the shape of the top and bottom surface is the same.

In one embodiment the dosage unit is a three-dimensional body of cylindrical form with a flat bottom. At one end of the body (the bottom surface) the cylindrical body has a plan (flat) surface and the edges between the lateral surface and the bottom surface have an angle between 45° and 110°. At the other end of the cylindrical body (the top surface) the dosage unit (soft chew) has at least one concave, rounded edge.

In one embodiment the soft chew is in a cylindrical form with a flat bottom at one end and round, concave edges at the other end of the cylinder.

In one embodiment the dosage unit is a three-dimensional body of cone form with a flat bottom and round, concave edges at the top end of the cone.

In one embodiment the diameter of the top and bottom circular surface of the dosage unit in cylinder or cone form is between 5 and 50 mm. In one embodiment the diameter of the top surface is between 5 and 10 mm, and of the bottom surface between 5 and 15 mm. In one embodiment the diameter of the top circular surface is smaller than the diameter of the bottom circular surface.

In another embodiment the diameter of the top and bottom circular surface of the dosage unit in cylinder or cone form is between 5 and 50 mm. In one embodiment the diameter of the top surface is between 15 and 30 mm, and of the bottom surface between 15 and 35 mm. In one embodiment the diameter of the top circular surface is smaller than the diameter of the bottom circular surface.

In one embodiment the dosage unit (e.g. soft chew) has an imprint on at least one surface of the dosage unit. In a specific embodiment this imprint is on the lateral area of the dosage unit. In another embodiment the imprint is on the top surface of the dosage unit. Such imprint can be e.g. letters, numbers, logos or symbols etc. In one embodiment there is an imprint on the bottom surface.

In another embodiment the dosage unit has a (cross) score or groove on one of the surfaces. This cross score has the effect that it facilitates the dividing of the dosage unit and by this, allows more exact dosing of the active pharmaceutical ingredient according to the body weight of the patient or animal.

Examples of such dosage units, e.g. soft chews are illustrated in FIG. 3 *a-g*.

The semi-plastic pharmaceutical dosage unit comprises the same active ingredients, dry and liquid components and forming agents as described earlier. Especially preferred are semi-plastic pharmaceutical dosage units e.g. soft chewable pharmaceutical dosage units comprising isoxazolines, especially is 4-[5-(3,5-Dichlorophenyl)-5-trifluoromethyl-4,5-dihydroisoxazol-3-yl]-2-methyl-N-[(2,2,2-trifluoro-ethyl-carbamoyl)-methyl]-benzamide (CAS RN [864731-61-3])—Compound A. Such semi-plastic pharmaceutical compositions are useful for the control of parasites, especially ectoparasites, especially ticks and fleas and can therefore be used in the manufacture of a medicament for controlling a parasitic insect, acarid or nematode infestation of an animal.

The amounts of each of the components in the dosage unit may be varied considerably, depending upon the nature of the pharmaceutically active ingredients, the weight and condition of the subject treated. Those of ordinary skill in the art will be able to adjust dosage amounts for particular pharmaceutically active ingredients in light of the teachings of this disclosure.

Generally, however, the pharmaceutically active ingredients may be provided by range in weight based on the total weight of the composition from about 0.001% to 75% (w/w), more preferably 0.1% to 40%.

In general, the semi-plastic pharmaceutical dosage unit according to the invention (e.g. soft chew) comprises an effective amount of the active pharmaceutical ingredients, meaning a non-toxic but sufficient amount to provide the desired therapeutic, prophylactic or control effect. A person skilled in the art using routine experimentation may determine an appropriate "effective" amount in any individual case. Such an amount will depend on the age, condition, weight and type of the patient or target animal. The dosage units, such as soft chews may be formulated to contain an amount of active ingredients that is adjusted to animals or patients in a specific weight range. The animals may receive a dosage every 2, 3, 4, 5 or 6 months or receives a monthly, weekly or daily dosage. In one embodiment the animal receives a dosage every 2 months. In another embodiment the animal receives a dosage every 3 months. In another embodiment the animal receives a dosage every 6 months. The treatment can, for example, be continuing or seasonal.

In general the dosage unit according to the current invention can be administered to humans and all species of animals. In one embodiment the animal is a mammal. The recipient of the dosage unit may be a livestock animal, e.g. sheep, cattle, pig, goat or poultry; a laboratory test animal, e.g. guinea pig, rat or mouse; or a companion animal, e.g. dog, cat, rabbit, ferret or horse. The dosage unit according to the invention is especially suitable for use in companion animals, e.g. dogs, cats or ferrets.

As used herein, the term "w/w" designates weight/weight, the term "w/v" designates weight/volume. As used herein, % w/w represents the percentage by weight of an ingredient in the recipe of the dosage unit.

Example 1

| Soft chew formulations | |
|---|---|
| | w/w % |
| Formulation A | |
| Active ingredient | 8.93 |
| Flavour | 20.00 |
| Sucrose | 7.00 |
| Corn starch (filler) | 15.77 |
| Sodium lauryl sulphate | 2.00 |
| Sodium pamoate | 2.50 |
| Magnesium stearate | 0.75 |
| Aspartame | 0.25 |
| Glycerol | 7.50 |
| Soybean oil (0.1% BHT-stabilized) | 18.30 |
| Polyethylene glycol 3350 | 17.00 |

-continued

Soft chew formulations

| | w/w % |
|---|---|
| Formulation B | |
| Active ingredient | 8.93 |
| Flavour | 20.00 |
| Sucrose | 7.00 |
| Corn starch (filler) | 20.77 |
| Sodium lauryl sulphate | 2.00 |
| Sodium pamoate | 2.00 |
| Magnesium stearate | 0.75 |
| Aspartame | 0.25 |
| Glycerol | 7.50 |
| Soybean oil (0.1% BHT-stabilized) | 12.30 |
| Polyethylene glycol 3350 | 18.50 |
| Formulation C | |
| Active ingredient | 8.93 |
| Flavour | 10.00 |
| Sucrose | 20.50 |
| Corn starch (filler) | 20.27 |
| Sodium lauryl sulphate | 2.00 |
| Sodium pamoate | 2.00 |
| Magnesium stearate | 0.75 |
| Aspartame | 0.25 |
| Glycerol | 4.00 |
| Soybean oil (0.1% BHT-stabilized) | 12.80 |
| Polyethylene glycol 3350 | 18.50 |
| Formulation D | |
| Active ingredient | 13.64 |
| Flavour | 20.00 |
| Sucrose | 7.00 |
| Corn starch (filler) | 16.06 |
| Sodium lauryl sulphate | 2.00 |
| Sodium pamoate | 2.00 |
| Magnesium stearate | 0.75 |
| Aspartame | 0.25 |
| Glycerol | 7.50 |
| Soybean oil (0.1% BHT-stabilized) | 12.30 |
| Polyethylene glycol 3350 | 18.50 |
| Formulation E | |
| Active ingredient | 13.89 |
| Flavour | 20.00 |
| Sucrose | 7.00 |
| Corn starch (filler) | 15.81 |
| Sodium lauryl sulphate | 2.00 |
| Sodium pamoate | 2.00 |
| Magnesium stearate | 0.75 |
| Aspartame | 0.25 |
| Glycerol | 7.50 |
| Soybean oil (0.1% BHT-stabilized) | 12.30 |
| Polyethylene glycol 3350 | 18.50 |
| Formulation F | |
| Active ingredient | 13.89 |
| Flavour | 20.00 |
| Sucrose | 8.00 |
| Corn starch (filler) | 15.81 |
| Sodium lauryl sulphate | 2.00 |
| Sodium pamoate | 2.00 |
| Magnesium stearate | 0.75 |
| Aspartame | 0.25 |
| Glycerol | 6.50 |
| Soybean oil (0.1% BHT-stabilized) | 12.30 |
| Polyethylene glycol 3350 | 18.50 |

Active ingredient of Formulation A to F = 4-[5-(3,5-Dichlorophenyl)-5-trifluoromethyl-4,5-dihydroisoxazol-3-yl]-2-methyl-N-[(2,2,2-trifluoro-ethylcarbamoyl)-methyl]-benzamide Example 2

Preparation of the Dough with the Composition of Example 1

Dry powdery ingredients of the formulations of example 1 which exhibited aggregates were sieved. All dry powdery ingredients were weighed in and placed in the mixing vessel of a horizontal ploughshare mixing blender and mixed until the blend was visually practically homogeneous.

The defined amount of glycerol was added slowly followed by a short mixing. Soybean oil was added slowly followed again by a short mixing. The mixer was heated to a temperature inhibiting a too fast precipitation of the PEG which introduced in the next step.

The PEG 3350 was molten. The defined amount of the molten PEG was added quickly to the chew mixture in the horizontal ploughshare mixing blender, which was then mixed until the mixture was homogeneous and could be separated from the wall. The temperature of the resulting dough was 43° C. The mixture resembled a "cookie dough-like" appearance.

Example 3

Method of Manufacture for Soft Chews of Example 1 Using a Formax F6 Moulding Machine (Prior Art)

The dough was prepared as described in Example 2. The dough was transferred to the hopper of the Formax F6 forming machine and processed. After the forming, appearance of the soft chews was checked and the yield was calculated. A number of soft chews were deformed and the height of the soft chews was not consistent. The optical discard of small (ca. 0.8 g) and large (ca. 10.3 g) soft chews was more than 15%.

Example 4

Method of Manufacture for Soft Chews of Example 1 Rotary Moulding Machine According to the Invention The dough was prepared as described in Example 2. The dough was transferred to the hopper of the MFT-200 forming machine (Kruger & Salecker, Bad Schwartau, Germany).

The mixture was formed into individual chunks using the rotary moulding machine MFT-200 of Kruger & Salecker, Bad Schwartau with a forming roll out of PTFE (Teflon) containing cavities of cylindrical shape and the soft chews were, after hardening, packaged in holding containers. Weight, yield and appearance of the soft chews were checked.

As indicated in Table 1 to 4 the formed soft chews of were consistent in weight, size and shape and did not show any deformation and the processing in the rotary moulding machine went well. The optical discard of small (ca. 0.8 g) soft chews was 0% and of the large (ca. 10.3 g) soft chews was 2%. The yield after hardening was 97%.

A sample of 10 soft chews was taken after forming at beginning and end of the batch process and weighted. The weight of the soft chews was homogeneous after forming with the rotary forming machine.

TABLE 1

Individual weight (g) of small soft chews

| Soft chew No. | Time point 1 | Time point 2 |
|---|---|---|
| 1 | 0.789 | 0.792 |
| 2 | 0.789 | 0.782 |
| 3 | 0.780 | 0.793 |
| 4 | 0.794 | 0.790 |
| 5 | 0.788 | 0.786 |
| 6 | 0.781 | 0.782 |
| 7 | 0.790 | 0.790 |

TABLE 1-continued

Individual weight (g) of small soft chews

| Soft chew No. | Time point 1 | Time point 2 |
|---|---|---|
| 8 | 0.784 | 0.784 |
| 9 | 0.784 | 0.792 |
| 10 | 0.787 | 0.787 |
| Mean | 0.7866 | 0.7878 |
| SD | 0.00432 | 0.00418 |

TABLE 2

Individual weight (g) of large soft chews

| Soft chew No. | Time point 1 | Time point 2 |
|---|---|---|
| 1 | 10.03 | 10.08 |
| 2 | 10.03 | 10.03 |
| 3 | 10.04 | 10.05 |
| 4 | 9.94 | 10.16 |
| 5 | 9.99 | 10.10 |
| 6 | 10.09 | 10.09 |
| 7 | 9.86 | 9.97 |
| 8 | 10.08 | 9.94 |
| 9 | 10.09 | 10.04 |
| 10 | 10.01 | 10.00 |
| Mean | 10.0159 | 10.046 |
| SD | 0.07202 | 0.06535 |

The dimension of 10 sampled soft chews before packaging was measured and the appearance was evaluated. The sampled small and large soft chews had consistent dimensions and had a uniform shape without deformation. Therefore they are suitable for individual packaging in blisters.

TABLE 3

Dimensions (mm) of individual small soft chews

| Soft Chew No. | Height | Diameter at top | Diameter at bottom |
|---|---|---|---|
| 1 | 8.23 | 8.72 | 11.48 |
| 2 | 8.34 | 8.34 | 10.65 |
| 3 | 8.23 | 8.71 | 10.58 |
| 4 | 8.22 | 8.98 | 10.72 |
| 5 | 8.19 | 8.72 | 10.40 |
| 6 | 8.30 | 8.88 | 10.90 |
| 7 | 8.20 | 8.71 | 10.60 |
| 8 | 8.13 | 8.77 | 10.82 |
| 9 | 8.21 | 8.82 | 10.82 |
| 10 | 8.28 | 8.70 | 10.62 |
| Mean | 8.233 | 8.735 | 10.759 |
| SD | 0.06000 | 0.16614 | 0.29175 |

TABLE 4

Dimensions (mm) of individual large soft chews

| Soft Chew No. | Height | Diameter at top | Diameter at bottom |
|---|---|---|---|
| 1 | 16.01 | 23.17 | 27.03 |
| 2 | 15.51 | 22.79 | 26.58 |
| 3 | 16.29 | 22.91 | 27.07 |
| 4 | 16.01 | 23.39 | 27.33 |
| 5 | 16.12 | 23.58 | 26.47 |
| 6 | 16.46 | 22.86 | 27.37 |
| 7 | 16.38 | 23.50 | 27.15 |
| 8 | 16.28 | 23.66 | 27.54 |
| 9 | 16.13 | 23.40 | 27.19 |
| 10 | 16.17 | 23.93 | 27.34 |
| Mean | 16.136 | 23.319 | 27.107 |
| SD | 0.26542 | 0.37743 | 0.34322 |

What is claimed is:

1. A soft chewable veterinary pharmaceutical product for oral administration,
wherein the soft chewable veterinary pharmaceutical product is obtainable by a process wherein the soft chewable veterinary pharmaceutical product is formed with a rotary moulding machine, comprising the steps of:
a) mixing at least one active pharmaceutical ingredient with one or more components wherein the components are dry components and liquid components to prepare a premix,
b) heating a polyethylene glycol forming agent until melting,
c) mixing the premix and the polyethylene glycol forming agent together to form a dough,
d) feeding the dough into a container connected with a rotary moulding machine; and
e) forming a soft chewable veterinary pharmaceutical product for oral administration in a rotary moulding machine,
wherein the liquid component comprises one or more oils and the polyethylene glycol forming agent is solid at room temperature and has a melting point between 45° C. and 100° C.;
wherein the temperature of the dough in step d) is between 35° C. and 45° C.; and
wherein the rotary moulding machine does not have a knockoff mechanism or a punch mechanism;
wherein the active pharmaceutical ingredient is 4-[5-(3, 5-Dichlorophenyl)-5-trifluoromethyl-4,5-dihydroisoxazol-3-yl]-2-methyl-N-[(2,2,2-trifluoro-ethylcarbamoyl)-methyl]-benzamide; and
wherein the soft chewable veterinary pharmaceutical product has concave edges and has a weight of about 2 g or less or has a weight of more than about 10 g.

2. The soft chewable veterinary pharmaceutical product for oral administration according to claim 1, wherein soft chewable veterinary pharmaceutical product is of cylindrical form.

3. A method of controlling a parasitic insect, acarid or nematode infestation of an animal comprising administering to the animal an effective amount of the soft chewable veterinary pharmaceutical product for oral administration of claim 1.

* * * * *